United States Patent

Takahashi et al.

[11] 4,215,049
[45] Jul. 29, 1980

[54] ANTITUMORIGENIC LACTONE DERIVATIVE

[75] Inventors: Takeyoshi Takahashi, Tokyo; Hirozumi Eto, Yokohama; Osamu Yoshioka, Yono, all of Japan

[73] Assignee: Nippon Kayaku Kabushiki Kaisha, Tokyo, Japan

[21] Appl. No.: 874,945

[22] Filed: Feb. 3, 1978

[30] Foreign Application Priority Data

Feb. 10, 1977 [JP] Japan .................. 52/13654

[51] Int. Cl.$^2$ ........................................... C07D 307/93
[52] U.S. Cl. ............................. 260/343.3 R; 424/279
[58] Field of Search ................................. 260/343.3 R

[56] References Cited
PUBLICATIONS

Dolejs et al., Chem. Abstracts, vol. 58, 10244.
Chem. Abstracts, 1967–1971, Subject Index.
Kupchan et al., J. Org. Chem., vol. 38, No. 12, 1973, p. 2189 and vol. 38, pp. 2189–2196.
Holub et al., Collection Czchoslov. Chem. Commun., 42, 1053–1064, 1976.
Drozdz, Collection Czchoslov Chem. Commun., 37, 1546, 1972.

*Primary Examiner*—Natalie Trousof
*Assistant Examiner*—Jane T. Fan
*Attorney, Agent, or Firm*—Stevens, Davis, Miller & Mosher

[57] ABSTRACT

There are disclosed novel compounds which are extracted with an organic solvent from *Eupatorium sachalinense* belonging to the genus Eupatorium and isolated by normal separating and refining procedures, the compounds being expressed by the general formula:

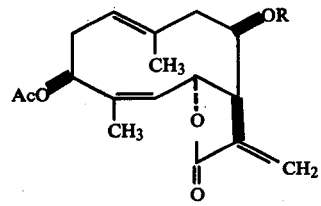

where R is

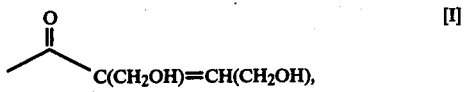

a pale yellowish oily substance having an optical rotation of $[\alpha]_D^{24} -121°$ (C=0.75, ethanol), a molecular weight of 420 estimated from peak value in mass spectrum measurement (theoretical value: 420), a molecular formula of $C_{22}H_{28}O_8$, an end absorption at 210 mm ($\epsilon$:14800) in ultraviolet absorption spectrum, peaks in infrared absorption spectrum by liquid film method at the frequencies (cm$^{-1}$) of 3400, 2920, 2845, 1760, 1740, 1705, 1658, 1440, 1370, 1325, 1220–1280, 1180, 1133, 1107, 1070, 1020, 970, 881, 840, 819, 788, 758, 710, 662, 630, 607 and 582, assignments of respective protons in NMR spectrum ($\delta$,CDCl$_3$) at C$_6$—H=5.96 (1H, dd, J=11,2), C$_4$—CH$_3$=1.80 (3H, d, J=1), C$_{10}$—CH$_3$=1.84 (3H, s), C$_{3'}$—H=6.90 (1H, t, J=5.5), C$_{4'}$—H=4.37 (2H, d, J=5.5), C$_{5'}$—H=4.31 (2H, s), exo CH$_2$=5.79,6.33 (1H, d, J=2), COCH$_3$=2.12 (3H, s);

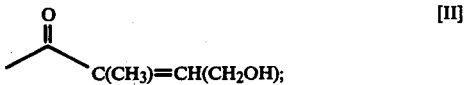

or [III] hydrogen; and a process for the preparation of these compounds.

These compounds are found to have not only inhibitive effects, even in a low concentration, against experimental cancer cells (HeLa) but also considerable life prolonging effects in in vitro experiments on mice inoculated with *Ehrlich ascites*, suggesting similar effects on malignant tumors in humans.

1 Claim, 3 Drawing Figures

ANTITUMORIGENIC LACTONE DERIVATIVE

BACKGROUND OF THE INVENTION

This invention relates to novel compounds expressed by the following general formuula:

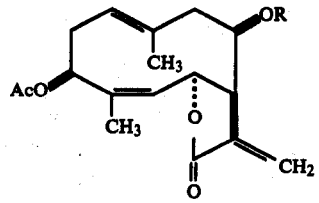

[I]

where R is

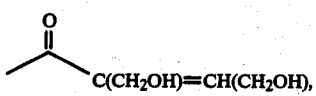

$C(CH_2OH)=CH(CH_2OH)$, a pale yellowish oily substance having an optical rotation of $[\alpha]_D^{24} - 121°$ (C=0.75, ethanol), a molecular weight of 420 estimated from peak value in mass spectrum measurement (theoretical value: 420), a molecular formula of $C_{22}H_{28}O_8$, an end absorption at 210 mm ($\epsilon$:14800) in ultraviolet absorption spectrum, peaks in infrared absorption spectrum by liquid film method at the frequencies (cm$^{-1}$) of 3400, 2920, 2845, 1760, 1740, 1705, 1658, 1440, 1370, 1325, 1220–1280, 1180, 1133, 1107, 1070, 1020, 970, 881, 840, 819, 788, 758, 710, 662, 630, 607 and 582, assignments of respective protons in NMR spectrum ($\delta$, CDCl$_3$) at C$_6$—H=5.96 (1H, dd, J=11,2), C$_4$—CH$_3$=1.80 (3H, d, J=1), C$_{10}$—CH$_3$=1.84 (3H, s), C$_{3'}$—H=6.90 (1H, t, J=5.5), C$_{4'}$—H=4.37 (2H, d, J=5.5), C$_{5'}$—H=4.31 (2H, s), exo CH$_2$=5.79,6.33 (1H, d, J=2), COCH$_3$=2.12 (3H, s);

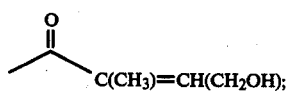

$C(CH_3)=CH(CH_2OH)$;

[II]

or [III] hydrogen; and a process for the preparation of these substances.

Recently, analytical research into the components of the various plants belonging to the genus Eupatorium has been pursued by Kupchan et al (J. Org. Chem. 38, 1260, 2189 (1973)), and various compounds having a significant antitumorigenic effect have been isolated. Among these compounds, those having the germacrane skeleton include the following:

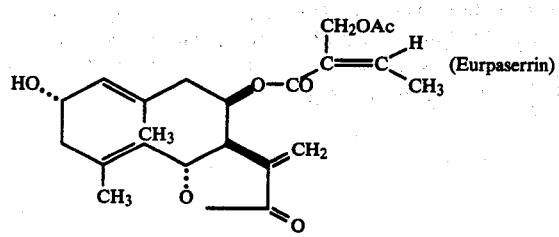

(Eurpaserrin)

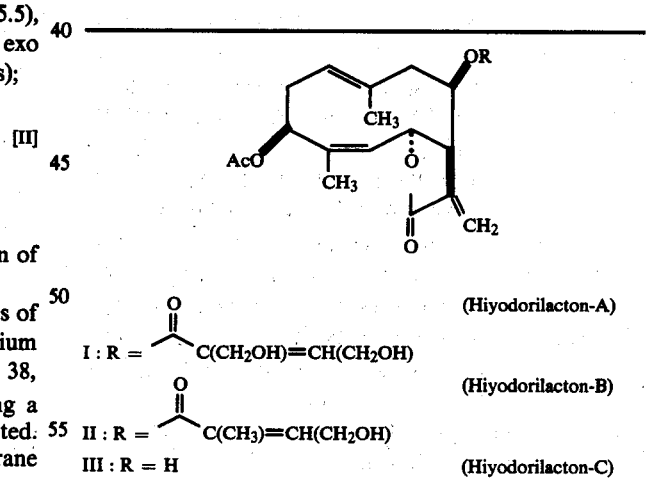

and it is known that these compounds show an inhibitory effect against growth of the cancer cells in the in vitro tests on the experimental cancer cells.

As a result of many experimental separation and refining of the extracts from *Eupatorium sachalinense*, a plant belonging to the genus Eupatorium, the present inventors have succeeded in isolating three novel substances (I, II and III) of the germacrane system, and it was clarified from various spectral analytical data and chemical reactions that these substances have the following chemical structures:

The compound I obtained from the plants belonging to Eupatorium is a stereoisomer of eucannabinolide which is described by B. Drozdz et al (Collection Czechoslov Chem. Commun. 37 1546 1972)) and by M. Holub et al (ibid 42 1053 (1977)) and of eupaformosanin which was described by Kuo-Hsing et al (Phytochemistry 16 1068 (1977)), eucannabinolide and eupaformosanin having the structures as indicated below.

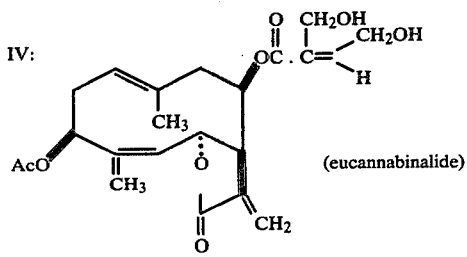

IV: (eucannabinalide)

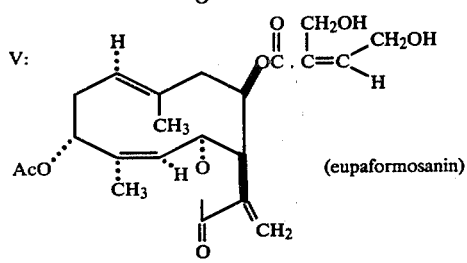

V: (eupaformosanin)

Compound I is same as the compounds IV and V in plane structure but has the acetoxyl group on the mother ring in beta-position in contrast the alpha location of the counterpart in compound V.

Upon comparing the physical properties of compound I with the corresponding data for compound IV given by B. Drozdz et al, the two compounds are found to have same appearance, optical rotation and molecular weight and exhibit peaks at similar frequencies in their infrared absorption spectra. However, in NMR spectrum, the hydrogen signal of the methylene group at C—4' of the side chain appears at δ4.37 (d, J=5.5) with compound I, in contrast to δ4.00 (d, J=6.0) of compound IV.

Compounds I and IV are identical with respect to the structure of the mother ring but they are considered to be stereoisomers with respect to the side chain.

Although it is not known whether the compounds IV and V have anticarcinogenic activity, the compounds I to III according to the present invention have been ascertained to have not only high inhibitory effect against growth of experimental cancer cells (HeLa) when used even in a low concentration, but also considerable life prolonging effect in the in vitro experiments on mice inoculated with Ehrlich ascites cancer cells, suggesting availability of these substances as a medicine for malignant tumors in humans.

The compounds I to III are contained throughout the body of the plant including root, stems and leaves, but since they exist in greater concentration in the leaves, it is advantageous to use the leaves as their extraction source.

SUMMARY OF THE INVENTION

It is an object of the present invention to provide the novel compounds mentioned above and a process for the preparation thereof.

According to the present invention, there is provided a compound expressed by the general formula:

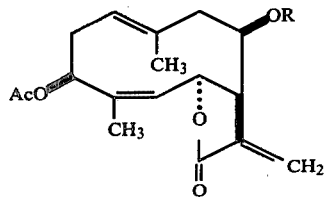

where R is

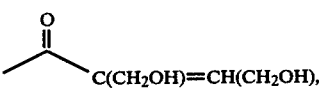

$C(CH_2OH)=CH(CH_2OH)$, [I]

a pale yellowish oily substance having an optical rotation of $[\alpha]_D^{24} -121°$ (C=0.75, ethanol), a molecular weight of 420 estimated from peak value in mass spectrum measurement (theoretical value:420), a molecular formula Of $C_{22}H_{28}O_8$, an end absorption at 210 mm (ε:14800) in ultraviolet absorption spectrum, peaks in infrared absorption spectrum by liquid film method at the frequencies (cm$^{-1}$) of 3400, 2920, 2845, 1760, 1740, 1705, 1658, 1440, 1370, 1325, 1220–1280, 1180, 1133, 1107, 1070, 1020, 970, 881, 840, 819, 788, 758, 710, 662, 630, 607 and 582, assignments of respective protons in NMR spectrum (δ, CDCl$_3$) at $C_6$—H=5.96 (1H, dd, J=11,2), $C_4$—$CH_3$=1.80 (3H, d, J=1), $C_{10}$—$CH_3$=1.84 (3H, s), $C_{3'}$—H=6.90 (1H, t, J=5.5), $C_{4'}$—H=4.37 (2H, d, J=5.5), $C_{5'}$—H=4.31 (2H, s), exo $CH_2$=5.79, 6.33 (1H, d, J=2), $COCH_3$=2.12 (3H, s);

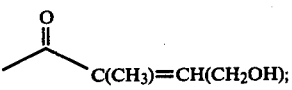

$C(CH_3)=CH(CH_2OH)$; [II]

or [III] hydrogen.

According to the invention, there is also provided a process for the preparation of the compound mentioned above, comprising extracting the compound with organic solvent from *Eupatorium sachalinense* belonging to the genus Eupatorium, followed by separation and refining.

Figure 1:
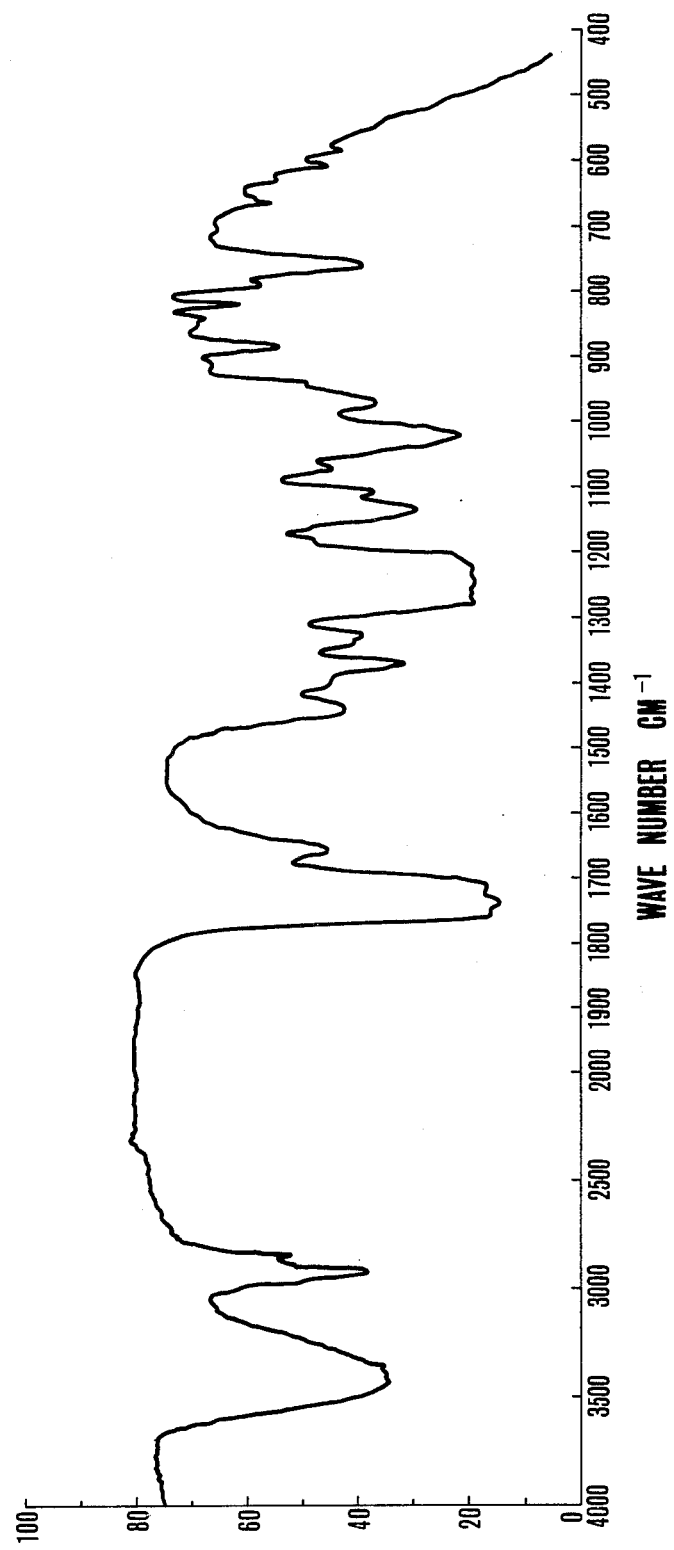
FIGS. 1 to 3 are infrared spectra of compounds I to 3, respectively.

The present invention will be illustrated more particularly by the following experiments and Example.

EXPERIMENTAL EXAMPLE 1

(a) Method of experiment

The roots (0.3 kg by half-dry weight), stalks (1.6 kg by half-dry weight) and leaves (2.1 kg by half-dry weight) were ground and extracted respectively with methanol. Each liquid extract was filtered and the filtrate was concentrated under reduced pressure to obtain an oily residue containing the object compounds.

(b) Results

The amounts (weight) of the oily materials obtained from the respective parts of the plant (*Eupatorium sachalinense*) and their effect against growth of the HeLa Cells were as shown in Table 1 below.

Table 1

| Extraction source | Weight (g) | Concentration | Inhibitory effect |
|---|---|---|---|
| Root | 12 | 200 μg/ml | 12.5% |
| Stalk | 47 | 200 μg/ml | 12.5% |
| Leaf | 99 | 35 μg/ml | 50% |

(Note) The inhibitory effect against growth of the HeLa cells was determined in the manner described below.

For producing the object substances from *Eupatorium sachalinense* according to the process of this invention, first the dried portions of *Eupatorium sachalinense* are extracted with an organic solvent at normal temperature or with heating and the liquid extract is concentrated under reduced pressure to obtain the primary extract.

The organic solvent used here may be, for example, an alcohol such as methanol, ethanol or propanol, a ketone such as acetone, methyl ethyl ketone or methyl isobutyl ketone, a halogenated hydrocarbon such as ethylene dichloride, chloroform or carbon tetrachloride, an aromatic hydrocarbon such as benzene, toluene or xylene, or an ester such as methyl acetate or ethyl acetate. However, since the dried portions of the plant used for the extraction still contain water, it is advantageous to use a volatile solvent miscible with water. Considering these conditions and economical availability, it is most advantageous to employ a hydrophilic organic solvent such as a lower alcohol or acetone, most preferably methanol.

Then the primary extract is cleared of the hydrophilic or non-hydrophilic impurities by means of solvent fractionation. As the solvent system used for this treatment, it is recommended to employ a suitable combination of a hydrocarbon or halogenated hydrocarbon with water, aqueous methanol or aqueous acetone.

For instance, as described in the Examples shown later, the primary extract is first mixed with chloroform and water and the fractionated chloroform layer is concentrated under reduced pressure to eliminate the hydrophilic impurities, and then in order to remove the non-hydrophilic impurities, the concentrate is distributed in a petroleum ether and a 10% aqueous methanol solution and the fractionated aqueous methanol layer are similarly concentrated, thereby obtaining a concentrate containing the object compounds. The latter operation may be accomplished by washing the primary extract with petroleum ether, but in this case, the refining efficiency is poor.

For separating the respective components from the thus obtained secondary extract, it is generally recommended to employ column chromatography using silica gel or alumina as adsorbent, but in some cases the object may be attained by using a simple batch type adsorption-elution method. It is also possible in certain cases to apply the adsorption method by omitting a part of the primary or secondary extraction process.

The eluent used for column chromatography is preferably a non-hydrophilic solvent such as chloroform, ethyl acetate ester, dichloroethane or benzene, which, if need be, is mixed with a small quantity of hydrophilic solvent such as methanol or acetone. In this case, it is advisable for obtaining better separation efficiency to gradually increase the ratio of the hydrophilic solvent to the non-hydrophilic solvent during the eluting treatment.

For attaining perfect separation of each component, it is suggested that chromatography be repeated for a particular fraction.

Finally, each fraction providing a single spot on the thin-layer chromatograph is fractionated and further concentrated and dried under reduced pressure, thereby obtaining the respective object components, compounds I, II and III.

The chemical properties and other characterizations of the object compounds of this invention are shown in Tables 2 and 3 below.

Table 2

Figure 2:
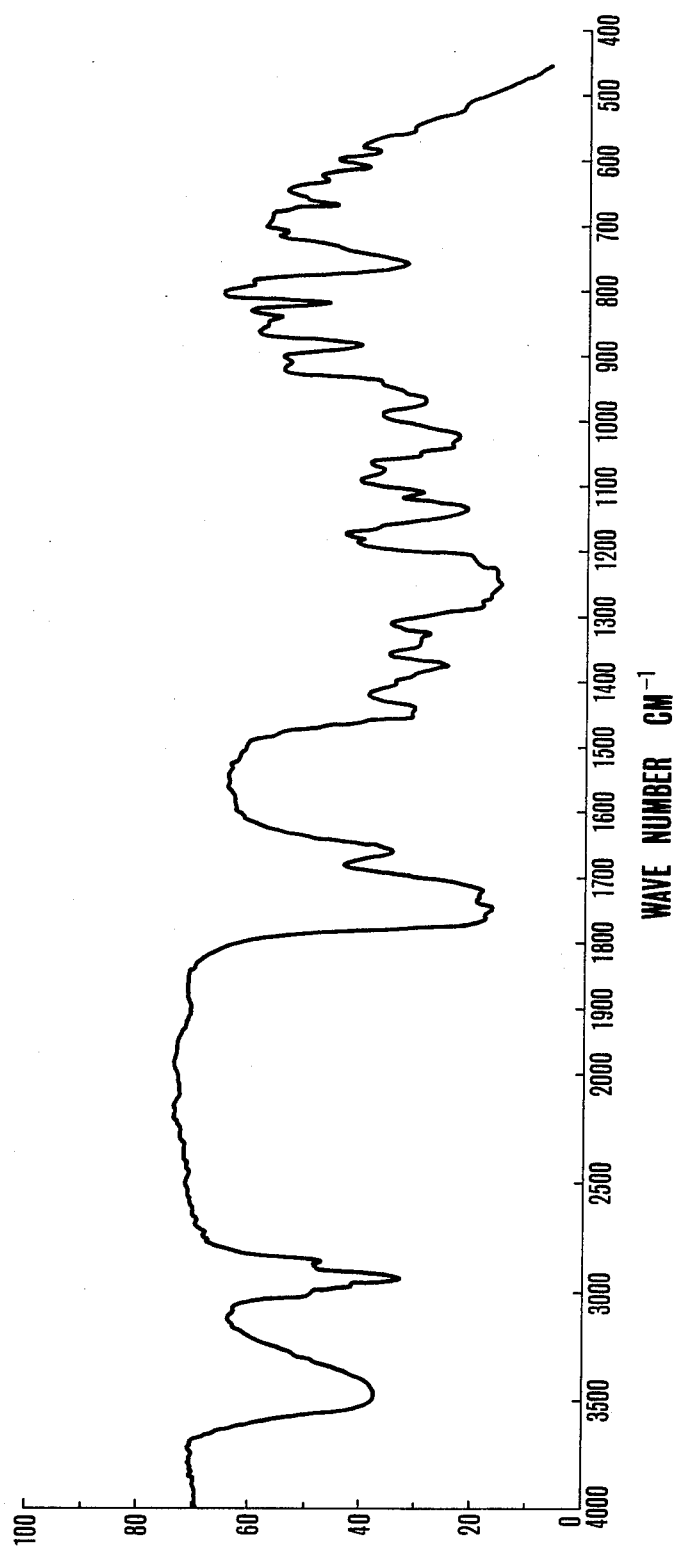
Figure 3:
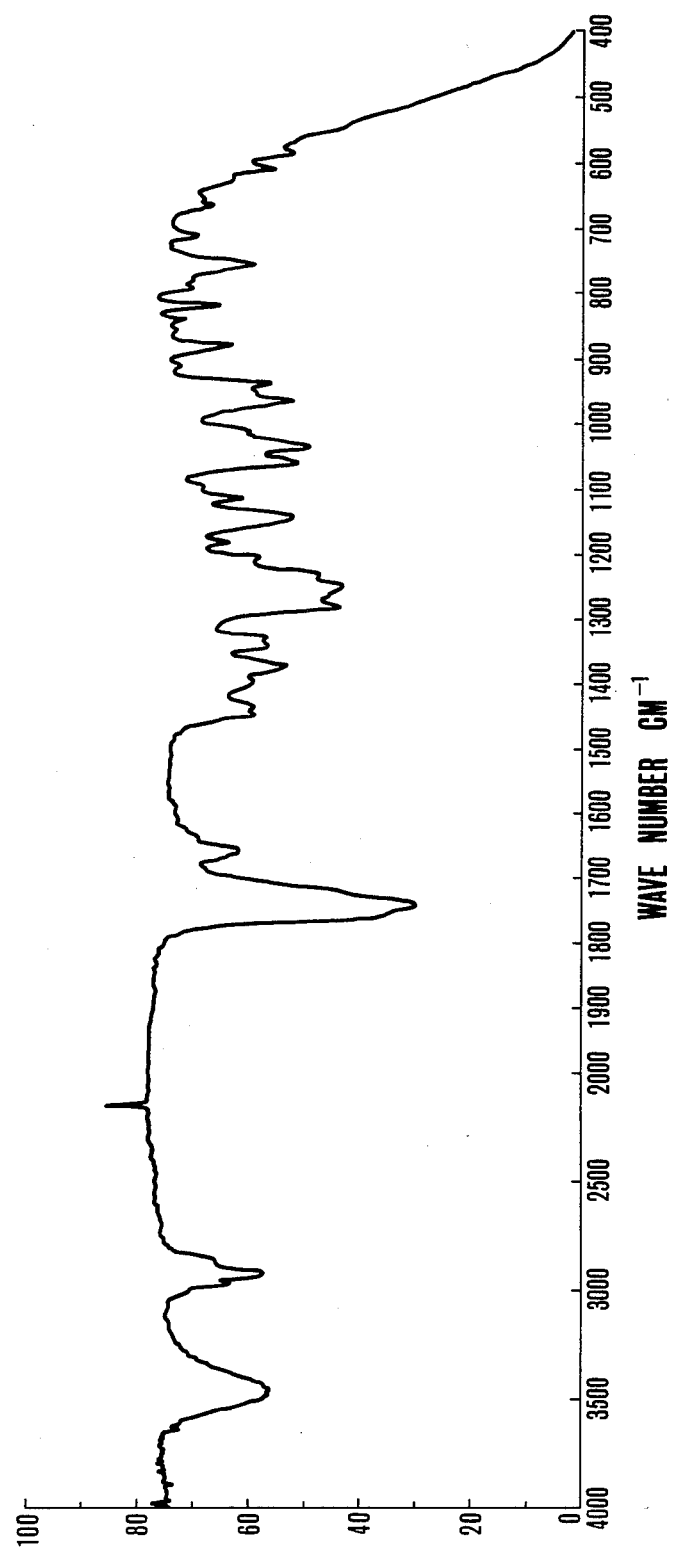

| Compound No. | External appearance | Optical rotation $[\alpha]_D^{24}$ Ethanol | Molecular weight measured by mass spectrum | Ultraviolet absorption spectrum | Infrared absorption spectrum | | | | | | |
|---|---|---|---|---|---|---|---|---|---|---|---|
| I | Colorless ~ Pale yellow Oily | −121° (C = 0.75) | Estimate from fragment peak : 420 Theoretical : 420 $C_{22}H_{28}O_8$ | End asorption 210 nm 1107 (ε:14800) | 3400 1440 1070 788 | 2920 1370 1020 758 | 2845 1325 970 710 | 1760 1220 881 662 | 1740 ~1280 840 630 (FIG. 1) | 1705 1180 819 607 | 1658 1133 582 |
| II | Colorless ~Pale yellow Oily | −140° (C = 0.67) | Found : 404 Theoretical : 404 $C_{22}H_{28}O_7$ | End absorption 210 nm (ε:30400) | 3460 1440 1110 790 | 2940 1375 1075 755 | 2850 1324 1020 710 | 1760 1225 970 667 | 1750 ~1235 883 630 (FIG. 2) | 1720 1180 840 608 | 1660 1138 820 585 |
| III | Colorless ~Pale yellow Oily | −109° (C = 0.91) | Found : 306 Theoretical : 304 $C_{17}H_{22}O_5$ | End absorption 210 nm (ε:14600) | 3460 1435 1110 817 580 | 2920 1370 1060 790 | 2860 1328 1033 753 | 1760 1280 962 710 | 1740 1250 940 664 (FIG. 3) | 1660 1180 880 625 | 1450 1140 840 607 |

Table 3

NMR spectrum: assignment of respective proton (δ)

[Structure diagram showing a molecule with positions labeled 1-10, CH₃ at position 6, AcO group, OR group, exo CH₂, with R defined as:

R = —C(=O)—C(CH₂OH)=CH(CH₂OH)  (I)  positions 1' 2' 5' 3' 4'

R = —C(=O)—C(CH₃)=CH(CH₂OH)  (II)  positions 1' 2' 5' 3' 4'

R = H  (III)]

| Compound No. | $C_6$—H | $C_4$—$CH_3$ | $C_{10}$—$CH_3$ | $C_{3'}$—H | $C_8$—H | $C_{4'}$—H | $C_{5'}$—H | Exo $CH_2$ | $COCH_3$ |
|---|---|---|---|---|---|---|---|---|---|
| I | 5.96 (1H, dd, J = 11, 2) | 1.80 (3H, d, J = 1) | 1.84 (3H, s) | 6.90 (1H, t, J = 5.5) | | 4.37 (2H, d, J = 5.5) | 4.31 (2H, s) | 5.79 6.35 (1H, d, J = 2) | 2.12 (3H, s) |
| II | 5.98 (1H, dd, J = 11, 3) | 1.80 (6H, s) | | 6.81 (1H, t, J = 6) | | 4.31 (2H, d, J = 6) | 1.80 (3H, s) | 5.79 6.36 (1H, d, J = 2) | 2.10 (3H, s) |
| III | 5.86 (1H, dd J = 11, 2) | 1.80 (3H, d, J = 1.5) | 1.90 (3H, s) | | 4.20 (1H, m, w ½ = 9) | | | 5.70 6.38 (1H, d, J = 2) | 2.07 (3H, s) |

(1) Inhibitory effect against HeLa $S_3$ cells (a) Method of experiment

The HeLa $S_3$ cells were spread on 6 cm-diameter plastic laboratory plates in the amount of $0.7 \times 10^5$ cells/plate and cultured by using an MEM medium containing 60 μg/ml of kanamycin and 10% calf serum. 2 days later, the medium was replaced with one containing the compounds of this invention. The cell population at that time was $1.58 \times 10^5$ cells/plat. After addition of the compounds, the cells were cultured for three days, and then, after removing the medium, the culture was washed with a physiological saline solution, treated with 0.05% trypsin at room temperature for about 15 minutes, and then pipetted and dispersed. The number of surviving cells was counted by a coal-tar counter, and percent inhibition was measured by counting the number of the living cells in the control section to determine $ID_{50}$.

Percent inhibition =

$$\left\{ 1 - \frac{\text{(Nr. of cells after culture with addition of compound (VI))} - \text{(Nr. of cells at the time of addition of compound (VI))}}{\text{(Nr. of cells in control section)} - \text{(Nr. of cells at the time of addition of compound (VI))}} \right\} \times 100$$

(b) Results

The results of the experiment were as shown in Table 4.

Table 4

| Compound No. | Inhibitory effect against growth of HeLa cells | | $ID_{50}$ (μg/ml) |
|---|---|---|---|
| | Centration (μg/ml) | Percent inhibition (%) | |
| I | 4 | 100 | 1.4 |
| | 2 | 74.9 | |
| | 1 | 29.4 | |
| II | 1.5 | 100 | 0.62 |
| | 0.75 | 57.0 | |
| | 0.375 | 28.4 | |

(2) Life-prolonging effect for mice suffering from *Ehrlich ascites* cancer (a) Method of experiment The mice of ICR/JCL species (♂, 5-week-old, 5 mice per group) were intraperitoneally inoculated with 2,000,000 pieces of *Ehrlich ascites* cancer cells, and the compounds of this invention were administered, starting 2 hours after inoculation, in the dosages shown in Table 5 below once a day for a total period of 10 days. The mice were observed for 50-days.

(b) Results

The experimental results were as shown in Table 5 below.

Table 5

| Compound No. | Life-prolonging effect for the mice suffering from Ebrlich ascites cancer | |
|---|---|---|
| | Dose mg/kg | Life prolongation rate* |
| I | 7.50 | 253 |
| | 15.0 | 232 |
| II | 7.50 | 159 |
| | 15.0 | 173 |
| III | 7.50 | 95 |
| | 15.0 | 108 |

*The "life prolongation rate" shows the average number of survival days of the drug treated groups as calculated with the average number of survival days of the control group being indexed as 100.

As apparent from the results shown in Table 4 and Table 5, the compounds I and II of this invention manifested not only a high inhibitory effect against growth of the cancer cells, with a low concentration (dose), in the in vitro tests on the experimental cancer (HeLa) cells but also a prominent life-prolonging effect for the mice afflicted with *Ehrlich ascites* cancer but administered with the compounds of this invention in comparison with the control mice. These results are suggestive of utility of these compounds for treatment of tumors in humans.

Although compound III is not so conspicuous in effect as the compounds I and II, it is useful as an intermediate intended to be transformed into the compounds I and II and associated compounds.

Now the process of this invention is described in further detail by way of the following examples.

EXAMPLE 1

The leaves of *Eupatorium sachalinense* (2.1 kg by half-dry weight) collected in August at Kita Saku-gen, Nagano-ken, were ground and then extracted with 1.2 liters of methanol divided in three portions. The exudates from the respective maceration treatments were filtered and the filtrates were combined and concentrated under reduced pressure to obtain 99 gr of an oily residue.

99 gr of this extract was divided into two layers with 3 liters of water and 4.4 liters of chloroform, and the solvent was distilled off from the chloroform layer under reduced pressure to obtain 30 gr of residue. This residue was dissolved in a mixed solution of 3.9 liters of petroleum ether and 2.9 liters of methanol/water (9/1) mixture, and after agitation, the methanol layer was fractionated. This methanol solution was concentrated under reduced pressure and water was removed from the residual solution by freeze-drying to obtain 7.8 gr of residue.

6.6 gr of this residue was dissolved in chloroform and the solution was passed through a column packed with 1 kg of silica gel to adsorb the object compound, and this was followed by elution first with chloroform, then with a chloroform-methanol solution and finally with methanol. The elution with a chloroform-methanol solution was performed by gradually increasing the methanol ratio.

(a) Of the eluted fraction, only the portion which had an Rf value of thin-layer chromatography (TLC) of 0.4 (using a chloroform (10)—methanol (1) developing solution) was collected and that portion was concentrated under reduced pressure and evaporated to dryness.

1.9 gr of the obtained residue was dissolved in a chloroform/acetone (4/1) mixed solution and passed through a column packed with 1.2 kg of silica gel to adsorb the object compound, and the adsorbate was eluted using a chloroform/acetone eluting solution whose chloroform:acetone ratio was gradually increased from an initial 4:1 to final 2:1, and the fraction containing the eluted-out object compound was gathered, concentrated under reduced pressure and dried.

There was consequently obtained 1.4 gr of a colorless oily substance (compound I) having the following properties: $[\alpha]_D^{24}$(EtOH, C=0.75):$-121°$; IR (liquid film) cm$^{-1}$:3400, 1760, 1740, 1705, 1658.

(b) The fraction portion having a TLC Rf value of 0.6 (using a chloroform (10)/methanol (1) developing solution) was collected, concentrated under reduced pressure and evaporated to dryness, and 1.4 gr of this residue was dissolved in a small amount of a chloroform/acetone (10/1) mixed solution and passed through a column packed with 1 kg of silica gel to adsorb the object compound, and the adsorbate was eluted using a chloroform/acetone (10/1) eluting solution, whereby a fraction containing compound II (TLC Rf: 0.6 (using a chloroform (5)/acetone (2) developing solution)) and then a fraction containing compound III (TLC Rf: 0.7 (using a chloroform (5)/acetone (2) developing solution)) were eluted out. These fractions were concentrated under reduced pressure to obtain 0.9 gr of a colorless oily product of compound II ($[\alpha]_D^{24}$ (EtOH, C=0.67):$-140°$; IR (liquid film) cm$^{-1}$:3460, 1760, 1750, 1720, 1660) and 0.17 gr of a colorless oily product of compound III ($[\alpha]_D^{24}$ (EtOH, C=0.91):$-109°$; IR (liquid film) cm$^{-1}$:3460, 1760, 1740, 1660).

What is claimed is:

1. Hiyodorilacton-B having the formula:

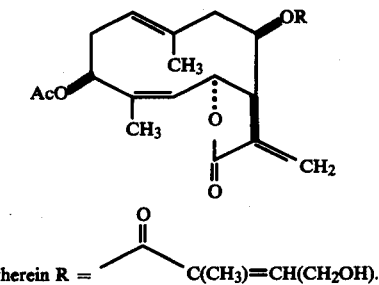

wherein R = $C(CH_3)=CH(CH_2OH)$.

* * * * *